US011684283B2

(12) United States Patent
Langley, II et al.

(10) Patent No.: US 11,684,283 B2
(45) Date of Patent: *Jun. 27, 2023

(54) SYSTEMS AND METHODS FOR DETECTING PHYSICAL CHANGES WITHOUT PHYSICAL CONTACT

(71) Applicant: Life Detection Technologies, Inc., Sunnyvale, CA (US)

(72) Inventors: John B. Langley, II, Half Moon Bay, CA (US); Guy McIlroy, Los Gatos, CA (US)

(73) Assignee: Life Detection Technologies, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/546,679

(22) Filed: Dec. 9, 2021

(65) Prior Publication Data

US 2022/0095943 A1 Mar. 31, 2022

Related U.S. Application Data

(63) Continuation of application No. 16/824,182, filed on Mar. 19, 2020, now Pat. No. 11,253,163, which is a (Continued)

(51) Int. Cl.
*G01R 29/12* (2006.01)
*A61B 5/05* (2021.01)
(Continued)

(52) U.S. Cl.
CPC .............. *A61B 5/05* (2013.01); *A61B 5/7278* (2013.01); *A61B 5/742* (2013.01);
(Continued)

(58) Field of Classification Search
CPC ........... A61B 5/05; A61B 5/725; A61B 5/742; A61B 5/746; A61B 5/7203; A61B 5/0402;
(Continued)

(56) References Cited

U.S. PATENT DOCUMENTS 4,182,315 A 1/1980 Vas et al.
4,788,869 A 12/1988 Li
(Continued)

FOREIGN PATENT DOCUMENTS

CN 1424577 A 6/2003
CN 1630822 A 6/2005
(Continued)

OTHER PUBLICATIONS

Extended European Search Report received for related European Patent Application No. 17744973.3 dated Aug. 21, 2019, 8 pages.
(Continued)

*Primary Examiner* — Thang X Le
(74) *Attorney, Agent, or Firm* — Weaver IP L.L.C.

(57) ABSTRACT

Systems and methods are provided for detecting and analyzing changes in a body. A system includes an electric field generator, an external sensor device, a quadrature demodulator, and a controller. The electric field generator is configured to generate an electric field that associates with a body. The external sensor device sends information to the electric field generator and is configured to detect a physical change in the body in the electric field, where the physical change causes a frequency change of the electric field. The quadrature demodulator receives the electric field from the electric field generator and is configured to detect the frequency change of the electric field and to produce a detected response. The controller, coupled to the electric field generator, is configured to output a frequency control
(Continued)

signal to the electric field generator and to modify the frequency of the electric field by adjusting the frequency control signal.

20 Claims, 10 Drawing Sheets

Related U.S. Application Data continuation of application No. 16/139,993, filed on Sep. 24, 2018, now Pat. No. 10,631,752, which is a continuation-in-part of application No. 15/418,328, filed on Jan. 27, 2017, now Pat. No. 10,080,507.

(60) Provisional application No. 62/287,598, filed on Jan. 27, 2016.

(51) Int. Cl.
| | |
|---|---|
| *A61B 5/00* | (2006.01) |
| *G01R 29/08* | (2006.01) |
| *A61B 5/024* | (2006.01) |
| *A61B 5/08* | (2006.01) |
| *A61B 5/113* | (2006.01) |
| *A61B 5/11* | (2006.01) |

(52) U.S. Cl.
CPC .......... *G01R 29/0814* (2013.01); *A61B 5/024* (2013.01); *A61B 5/0816* (2013.01); *A61B 5/1102* (2013.01); *A61B 5/113* (2013.01); *A61B 5/725* (2013.01); *A61B 5/7225* (2013.01)

(58) Field of Classification Search
CPC ................ A61B 5/04018; G01R 29/08; G01R 29/0814; G01N 27/22; G08B 21/02; G08B 21/0211
See application file for complete search history.

(56) References Cited

U.S. PATENT DOCUMENTS

| | | | |
|---|---|---|---|
| 4,958,638 A | 9/1990 | Sharpe et al. | |
| 5,434,887 A | 7/1995 | Osaka | |
| 6,020,784 A | 2/2000 | Fujii | |
| 6,339,623 B1 | 1/2002 | Iwamatsu | |
| 6,356,746 B1 | 3/2002 | Katayama | |
| 6,679,830 B2 | 1/2004 | Kolarovic et al. | |
| 6,686,800 B2 * | 2/2004 | Krupka ................ | H03F 1/56 330/69 |
| 7,109,726 B2 | 9/2006 | van Berkel | |
| 7,173,525 B2 | 2/2007 | Albert | |
| 7,242,728 B2 | 7/2007 | Kanazawa | |
| 7,383,071 B1 | 6/2008 | Russell et al. | |
| 7,445,605 B2 | 11/2008 | Overall et al. | |
| 7,885,700 B2 | 2/2011 | Clark et al. | |
| 7,887,708 B2 | 2/2011 | Chew | |
| 7,952,425 B2 | 5/2011 | Zhang et al. | |
| 8,057,388 B1 | 11/2011 | Russell et al. | |
| 8,274,386 B1 | 9/2012 | Dea et al. | |
| 8,604,772 B2 * | 12/2013 | Berkcan ................ | G01R 29/12 324/76.11 |
| 8,842,010 B2 | 9/2014 | Cehelnik | |
| 8,994,536 B2 | 3/2015 | Margon | |
| 9,035,778 B2 | 5/2015 | Howie et al. | |
| 9,060,745 B2 | 6/2015 | Su et al. | |
| 9,204,802 B2 | 12/2015 | Feldman et al. | |
| 9,285,889 B2 | 3/2016 | Bateman et al. | |
| 9,549,682 B2 | 1/2017 | Howie et al. | |
| 9,662,505 B2 * | 5/2017 | Kibler ................ | A61N 1/3727 |
| 9,685,996 B1 | 6/2017 | Thoen | |
| 9,921,706 B2 | 3/2018 | Kim et al. | |
| 10,080,507 B2 | 9/2018 | Langley, II et al. | |
| 10,631,752 B2 | 4/2020 | Langley, II et al. | |
| 11,026,593 B2 | 6/2021 | Langley, II et al. | |
| 2002/0013538 A1 | 1/2002 | Teller | |
| 2002/0032016 A1 | 3/2002 | Ji | |
| 2003/0021078 A1 | 1/2003 | van Berkel | |
| 2004/0100376 A1 | 5/2004 | Lye et al. | |
| 2004/0181703 A1 | 9/2004 | Lilja et al. | |
| 2004/0201384 A1 | 10/2004 | Berkel | |
| 2004/0250192 A1 | 12/2004 | Kanazawa | |
| 2004/0260346 A1 | 12/2004 | Overall et al. | |
| 2005/0104670 A1 | 5/2005 | Naviasky et al. | |
| 2005/0273218 A1 | 12/2005 | Breed et al. | |
| 2006/0154642 A1 | 7/2006 | Scannell, Jr. | |
| 2006/0158173 A1 | 7/2006 | Takiguchi | |
| 2006/0261818 A1 | 11/2006 | Zank et al. | |
| 2007/0055123 A1 * | 3/2007 | Takiguchi ................ | A61B 5/05 600/407 |
| 2007/0285296 A1 | 12/2007 | Bilhan | |
| 2008/0007445 A1 | 1/2008 | Leach, Jr. et al. | |
| 2008/0259043 A1 | 10/2008 | Buil et al. | |
| 2009/0048500 A1 | 2/2009 | Corn | |
| 2009/0079550 A1 * | 3/2009 | Makinen ............ | G09B 21/003 340/407.2 |
| 2009/0240160 A1 | 9/2009 | Thompson et al. | |
| 2009/0318779 A1 | 12/2009 | Tran | |
| 2010/0060350 A1 | 3/2010 | Zhang et al. | |
| 2010/0152600 A1 | 6/2010 | Droitcour et al. | |
| 2013/0267791 A1 | 10/2013 | Halperin et al. | |
| 2014/0055269 A1 | 2/2014 | Howie et al. | |
| 2014/0140444 A1 | 5/2014 | Onishi et al. | |
| 2014/0222110 A1 | 8/2014 | Kibler et al. | |
| 2015/0031964 A1 | 1/2015 | Bly et al. | |
| 2015/0057557 A1 | 2/2015 | Howie et al. | |
| 2015/0317002 A1 | 11/2015 | King-Smith et al. | |
| 2016/0148034 A1 | 5/2016 | Kremin et al. | |
| 2016/0179243 A1 | 6/2016 | Schwartz | |
| 2016/0187277 A1 | 6/2016 | Potyrailo et al. | |
| 2016/0187450 A1 * | 6/2016 | Heim ................ | G01R 35/005 324/603 |
| 2017/0209065 A1 | 7/2017 | Langley, II et al. | |
| 2018/0210582 A1 | 7/2018 | Kim et al. | |
| 2018/0368724 A1 | 12/2018 | Langley, II et al. | |
| 2019/0029556 A1 | 1/2019 | Langley, II et al. | |
| 2020/0214587 A1 | 7/2020 | Langley, II et al. | |

FOREIGN PATENT DOCUMENTS

| | | |
|---|---|---|
| CN | 101277645 A | 10/2008 |
| CN | 104644143 A | 5/2015 |
| EP | 2093588 A1 | 8/2009 |
| EP | 2886051 A1 | 6/2015 |
| FR | 2923150 A1 | 5/2009 |
| GB | 2062239 A | 5/1981 |
| JP | S60-142274 A | 7/1985 |
| JP | H07-288551 A | 10/1995 |
| JP | 2010-504155 A | 2/2010 |
| JP | 2010-537767 A | 12/2010 |
| JP | 2011-519288 A | 7/2011 |
| JP | 2015-091358 A | 5/2015 |
| JP | 2015-205045 A | 11/2015 |
| JP | 2016-020815 A | 2/2016 |
| JP | 2016-506524 A | 3/2016 |
| WO | 03/048789 A2 | 6/2003 |
| WO | 2015/174879 A1 | 11/2015 |
| WO | 2017132514 A1 | 8/2017 |
| WO | 2018/137977 A1 | 8/2018 |

OTHER PUBLICATIONS

Heartfelt tm Infant Vitals & Video Monitoring System, [online] (c) 2012 PREE Corporation, [retrieved on Sep. 20, 2012], Retrieved from the Internet: <URL:http://www.technophysics.com/technology/heartfelt_baby_monitor>, 2012, 4 pages.

International Search Report and Written Opinion for International Patent Application No. PCT/US2017/015345, dated Apr. 17, 2017, 9 pages.

International Search Report received in related PCT Application No. PCT/US19/52076 dated Dec. 13, 2019, 10 pages.

(56) References Cited

OTHER PUBLICATIONS

Non-Contact Monitor for Infants at Risk, SBIR/STTR.Award. [online] [retrieved on Sep. 20, 2012]. Retrieved from Internet: <URL:http://www.sbir.gov/sbirsearch/detail/156740>, 2 pages.
Office Action received in related Chinese Application No. 201780008413.6 dated Nov. 3, 2020, 11 pages.
Office Action received in related Japanese Patent Application No. 2018-539839 dated Oct. 13, 2020, 8 pages.
PREE Corporation's Heartfelt Infant Vitals and Video Monitoring System is Now in Pre-Sales, PREE Corporation Press Release, [online] [retrieved Sep. 20, 2012]. Retrieved from the Internet: <URL:http://www.businesswire.com/news/home/20120215006285/en/PREE-Corporations-Heartfelt-Infant-Vitals-Video-Monitoring>, Feb. 15, 2012, 1 page.
Standards for assessing, measuring and monitoring vital signs in infants, children and young people, (c) 2011 Royal College of Nursing, [online] [retrieved Sep. 20, 2012]. Retrieved from the Internet: <URL: http://www.rcn.org.uk/_data/assets/pdf_file/0004/114484/003196.pdf>, 2011, 16 pages.
Beardsmore-Rust, S.T. , "Remote applications of electric potential sensors in electrically unshielded environments", PhD. Thesis, University of Sussex. [online]. [retrieved on Sep. 20, 2012]. Retrieved from the Internet: <URL:http://sro.sussex.ac.uk/2407/1/Beardsmore-Rust%2C_Sam.pdf>, Apr. 2010, 185 pages.
Buckley, P., "Plessey EPIC sensor makes a heart monitor in a wristwatch", [online]. EE Times Europe, [retrieved on Sep. 20, 2012]. Retrieved from the Internet: <URL:http://www.eetimes.com/electronics-news/4372353/Plessey-reveals-EPIC-sensor-technology-to-create-a-heart-monitor-in-a-wristwatch>, May 6, 2012, 2 pages.
Connor, S., "EPIC—Introducing Plessey's multi award winning EPIC Sensor and its many applications", [online]. [retrieved Sep. 20, 2012]. Retrieved from the Internet: <URL:http://www.plesseysemiconductors.com/products/epic/technical/>, 2012, 5 pages.
Connor et al., "EPIC: A New Epoch in Electric Potential Sensing", [online]. [retrieved on Sep. 20, 2012]. Retrieved from the Internet: <URL:http://www.sensorsmag.com/sensors/electric-magnetic/epic-a-new-epoch-electric-potential-sensing-8961 >, Sep. 1, 2011, 4 pages.
German-Sallo, Z., "Applications of Wavelet Analysis in ECG Signal Processing", PhD. Thesis, Technical University of Cluj-Napoca, 2005, 11 pages.
German-Sallo, Z., "Processing of ECG Signals Using Wavelet Analysis", Acta Electrotechnica, vol. 46(3), 2005, pp. 135-140.
Hui et al., "Monitoring vital signs over multiplexed radio by near-field coherent sensing", Nature Electronics, vol. 1, Jan. 2018, pp. 74-78.
Saritha et al., "ECG Signal Analysis Using Wavelet Transforms", Bulg. J. Phys., 35, 2008, pp. 68-77.
Venkataramanan, M., "Biosensor can monitor your heartbeat from a distance", [online]. (c) Copyright Reed Business Information Ltd. [retrieved on Sep. 20, 2012]. Retrieved from the Internet: <URL: http://www.newscientist.com/blogs/onepercent/2011/11/sensor-monitors-your-heartbeat.html>, Nov. 16, 2011, 6 pages.
Yan et al., "Verification of a non-contact vital sign monitoring system using an infant simulator", Con. Proc. IEEE Eng. Med. Biol. Soc. 2009, (Abstract Only), [online]. [retrieved on Sep. 20, 2012]. Retrieved from the Internet: <URL: http://www.ncbi.nlm.nih.gov/pubmed>, 2009, 1 page.
Yan et al., "Verification of a Non-Contact Vital Sign Monitoring System Using an Infant Simulator", Con. Proc. IEEE Eng. Med. Biol. Soc., 31st Annual International Conference of the IEEE EMBS, (Minneapolis, MN, Sep. 2-6, 2009, 2009, pp. 4836-4839.
Extended European Search Report received for European Patent Application No. 19866310.6, dated Jun. 10, 2022, 8 pages.
S. Gabriel, et al., "The dielectric properties of biological tissues: III. Parametric models for the dielectric spectrum of tissues," Phys. Med. Biol. 41 (1996) pp. 2271-2293.
S. Guha et al., "An 8 GHz CMOS Near Field Bio-sensor Array for Imaging Spatial Permittivity Distribution of Biomaterials," IEEE MTT-S International Microwave Symposium (IMS2014), 2014, pp. 1-4.
Ron, Kapusta et al., "Sampling Circuits That Break the kT/C Thermal Noise Limit" IEEE Journal of Solid-State Circuits, vol. 49, No. 8, Aug. 2014, 5 pages.
Chris D. Nikolopoulos, et al., "Auto Reconfigurable Patch Antenna for Biomedical Single Channel Multi-Frequency Microwave Radiometry Applications," Progress In Electromagnetics Research C, vol. 49 (2014), pp. 19-29.
Daniel Teichmann et al., "A Bendable and Wearable Cardiorespiratory Monitoring Device Fusing Two Noncontact Sensor Principles," IEEE Journal of Biomedical and Health Informatics, vol. 19, No. 3, May 2015, pp. 784-793.
Daniel Teichmann et al., "Noncontact Monitoring of Cardiorespiratory Activity by Electromagnetic Coupling," IEEE Transactions on Biomedical Engineering, vol. 60, No. 8, Aug. 2013, pp. 2142-2152.
Mikael Ekström et al., "Critical review of non-invasive respiratory monitoring in medical care," Medical & Biological Engineering & Computing • Aug. 2003, pp. 377-383.
Shahid, Malik et al., "Respiration Monitoring Using a Flexible Paper-based Capacitive Sensor," 2018 IEEE, 2018, pp. 1-4.
U.S. Appl. No. 16/824,182, filed Mar. 19, 2020, Langley, II et al.
U.S. Appl. No. 16/139,993, filed Sep. 24, 2018, Langley, II et al.
U.S. Appl. No. 15/418,328, filed Jan. 27, 2017, Langley, II et al.
TDC7200: Time-to-digital converter for time-of-flight (ToF) application for LIDAR and ultrasonic, Retrieved from the Internet URL: https://www.ti.com/product/TDC7200, published Jan. 8, 2015.
Office Action received for Japanese Patent Application No. 2021-540782, dated Apr. 18, 2023, 6 pages (4 pages of English Translation and 2 pages of Official Copy).

\* cited by examiner

SYSTEMS AND METHODS FOR DETECTING PHYSICAL CHANGES WITHOUT PHYSICAL CONTACT

CROSS-REFERENCE TO RELATED APPLICATIONS

This is a continuation application of U.S. patent application Ser. No. 16/824,182, filed Mar. 19, 2020, which is a continuation application of U.S. patent application Ser. No. 16/139,993, filed Sep. 24, 2018, which is a continuation-in-part application of U.S. patent application Ser. No. 15/418,328, filed Jan. 27, 2017, which claims the benefit of U.S. Provisional Patent Application No. 62/287,598, filed on Jan. 27, 2016. The entire contents of each application above are incorporated by reference herein in their entirety as though fully disclosed herein.

TECHNICAL FIELD

This application relates generally to the technical field of monitoring systems, and more particularly, to a monitoring system that detects physical changes without physical contact.

BACKGROUND OF THE INVENTION

The performance of a variety of monitoring systems may be affected by where a sensor or its parts are placed relative to a target (e.g., a human such as an adult, teen, child, or baby) that is being monitored. For example, certain monitoring systems may require a sensor to be in physical contact with a target and may further require a part (e.g., a power or data cable) to be connected from a sensor to a monitoring device. There may be other circumstances in which the sensor might be used to detect changes in occupancy of a vehicle seat. In this case the sensor might also sense vital signs—e.g., pulse and/or respiration—of a seat occupant without direct physical contact.

Known monitoring systems require a sensor to be directly in contact with a target. For example, a traditional electrocardiogram (ECG) uses external electrodes to detect a patient's ECG signal. The external electrodes are located on the ends of cables and must be physically placed on a patient and near the patient's heart. This often necessitates the use of conductive materials that may be inconvenient to hook up and use, especially for long-term monitoring of a relatively active patient. These devices have significant limitations. For example, the patient must be physically connected to the device. If the patient wants to leave his or her bed, the device needs to be detached from, and then re-attached to the patient on his/her return, often by a highly trained staff member. The inconvenience and the delays associated with setting up such monitoring systems are also not well-suited for monitoring more active targets, for example, a baby in a crib or a person driving a vehicle. Although there are monitoring systems incorporated into devices such as wristbands and armbands they still typically need to be directly in contact with the target, and often provide inaccurate information and limited functionality.

Accordingly, there is a need for a monitoring system that does not require a sensor to be directly in contact with a target. There is also a need for a monitoring system that can assist in the management of a target's health, fitness, sleep and diet by monitoring physiological changes in a person's body. There is further a need for a monitoring system suitable for long-term use that can sense changes in a target and provide timely and appropriate diagnostic, prognostic and prescriptive information.

SUMMARY

This invention includes systems and methods that allow detection of physical changes within a body without physical contact with, or attachment to, the body. A body is a mass of matter distinct from other masses. Non-limiting examples of a body include, for example, a human's body, an animal's body, a container, a car, a house, etc. These changes might be physiological events such as cardiac function in an animal or changes in the properties of a bulk material such as grain in a silo. These changes could be dimensional changes such as those caused by the function of organs in an animal, or changes in the composition of the material such as water content in lumber.

A key feature of the measurement technique used in this instrument is that the measurement may be done over an extended volume such that the changes of multiple phenomena may be observed simultaneously. For example, sensing two separate but related physiological parameters (e.g., pulse and respiration) may be accomplished concurrently. The region sensed by this instrument may be changed by sensor element design within the instrument. A further extension of bulk sensing capability is the opportunity to use sophisticated computer signature recognition software, such as wavelet-based approaches, to separate individual features from the composite waveform.

This application relates to U.S. Pat. No. 9,549,682, filed on Oct. 30, 2014, which is explicitly incorporated by reference herein in its entirety. This application also relates to U.S. Pat. No. 9,035,778, filed on Mar. 15, 2013, which is explicitly incorporated by reference herein in its entirety.

Disclosed subject matter includes, in one aspect, a system for detecting and analyzing changes in a body. The system includes an electric field generator configured to produce an electric field. The system includes an external sensor device, coupled to the electric field generator, configured to detect physical changes in the electric field, where the physical changes affect amplitude and frequency of the electric field. The system includes a quadrature demodulator, coupled to the electric field generator, configured to detect changes of the frequency of the output of the electric field generator and produce a detected response that includes a low frequency component and a high frequency component. The system includes a low pass filter, coupled to the quadrature demodulator, configured to filter out the high frequency component of the detected response to generate a filtered response. The system includes an amplitude reference source configured to provide an amplitude reference. The system includes an amplitude comparison switch, coupled to the amplitude reference source and the electric field generator, configured to compare the amplitude reference and the amplitude of the electric field to generate an amplitude comparison. They system includes a signal processor, coupled to the low pass filter and the amplitude comparison switch, configured to analyze the filtered response and the amplitude comparison response.

Disclosed subject matter includes, in another aspect, a method for detecting and analyzing changes in a body. The method includes establishing an electric field around a desired area of detection with an electric filed generator. The method includes monitoring frequency of the electrical field with a quadrature demodulator. The method includes detecting changes in the frequency of the electric field with the quadrature demodulator. The method includes monitoring amplitude of the electric field. The method includes detecting changes in the amplitude of the electric field with an amplitude reference source.

Disclosed subject matter includes, in yet another aspect, a non-transitory computer readable medium having executable instructions operable to cause an apparatus to establish an electric field around a desired area of detection with an electric field generator. The instructions are further operable to cause the apparatus to monitor frequency of the electrical field with a quadrature demodulator. The instructions are further operable to cause the apparatus to detect changes in the frequency of the electric field with the quadrature demodulator. The instructions are further operable to cause the apparatus to monitor amplitude of the electric field. The instructions are further operable to cause the apparatus to detect changes in the amplitude of the electric field with an amplitude reference source.

Disclosed subject matter further includes, in yet another aspect, a system for detecting and analyzing changes in a body. The system includes an electric field generator, an external sensor device, a quadrature demodulator, and a controller. The electric field generator is configured to generate an electric field that associates with a body. The external sensor device sends information to the electric field generator and is configured to detect a physical change in the body in the electric field, where the physical change causes a frequency change of the electric field. The quadrature demodulator receives the electric field from the electric field generator and is configured to detect the frequency change of the electric field generated by the electric field generator and to produce a detected response. The controller is coupled to the electric field generator and is configured to output a frequency control signal to the electric field generator and to modify the frequency of the electric field by adjusting the frequency control signal.

Disclosed subject matter includes, in yet another aspect, a method for detecting and analyzing changes in a body. The method includes generating an electric field that associates with a body with an electric field generator. The method includes detecting a physical change in the body in the electric field with an external sensor device, where the physical change causes a frequency change of the electric field. The method includes monitoring and detecting changes in the frequency of the electric field and producing a detected response with a quadrature demodulator. The method includes receiving, by a controller, the detected response. The method includes outputting a frequency control signal to modify the frequency of the electric field associated with the body. The method includes modifying, by the electric field generator, the electric field associated with the body based on the frequency control signal.

Disclosed subject matter includes, in yet another aspect, a non-transitory computer readable medium having executable instructions operable to cause an apparatus to detect and analyze a change in a body. The instructions are further operable to cause the apparatus to generate an electric field that associates with a body. The instructions are further operable to cause the apparatus to detect a physical change in the body in the electric field, where the physical change causes a frequency change of the electric field. The instructions are further operable to cause the apparatus to monitor and detect changes in the frequency of the electric field and produce a detected response. The instructions are further operable to cause the apparatus to receive the detected response. The instructions are further operable to cause the apparatus to output a frequency control signal to modify the frequency of the electric field associated with the body. The instructions are further operable to cause the apparatus to modify the electric field associated with the body based on the frequency control signal.

Before explaining example embodiments consistent with the present disclosure in detail, it is to be understood that the disclosure is not limited in its application to the details of constructions and to the arrangements set forth in the following description or illustrated in the drawings. The disclosure is capable of embodiments in addition to those described and is capable of being practiced and carried out in various ways. Also, it is to be understood that the phraseology and terminology employed herein, as well as in the abstract, are for the purpose of description and should not be regarded as limiting.

These and other capabilities of embodiments of the disclosed subject matter will be more fully understood after a review of the following figures, detailed description, and claims.

It is to be understood that both the foregoing general description and the following detailed description are explanatory only and are not restrictive of the claimed subject matter.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

The manner in which materials behave in an alternating current ("AC") circuit usually is described in terms of the amount of energy stored in the material and the amount of energy dissipated in the material on a per cycle basis. Energy storage occurs in both electric and magnetic fields created by the current. Dissipation occurs in transformation, in the material, of electrical energy into thermal energy, i.e., heat. These properties can vary over a wide range depending on the material. In many materials the properties are predominantly one type.

Dissipation in some materials may be attributed to the magnetic field properties of a material and in other cases to the electric field properties. In more general cases, both of these mechanisms are present. Because of this, there is a convention in which the magnetic field storage properties and any related dissipation are combined in a vector sum and called permeability. Similarly, the vector sum of the electric field storage properties and associated dissipation is called permittivity. These vector sums are expressed as complex values in which the dissipation is the real component and field storage properties are the imaginary component. In the present disclosure, the aggregated change in properties of a body are detected and quantified by measuring changes in the body's electromagnetic properties.

Although the approach described here works by sensing changes in the electromagnetic properties, i.e. changes in both electric and magnetic properties, in some applications the significant changes occur in only one set of properties. For purposes of further discussion, the instrument in this invention detects changes in permittivity. Detection of any other suitable property or combination of properties that are appreciated by a person skilled in the art is also within the spirit and limit of the disclosed subject matter. The dissipative component of permittivity often is expressed as the loss tangent of the material, while the storage term is called capacitance. Measuring these properties is accomplished by sensing the change of phase and amplitude of an electric field generated by the instrument and caused by the aggregated properties of a body within the field.

Figure 1:
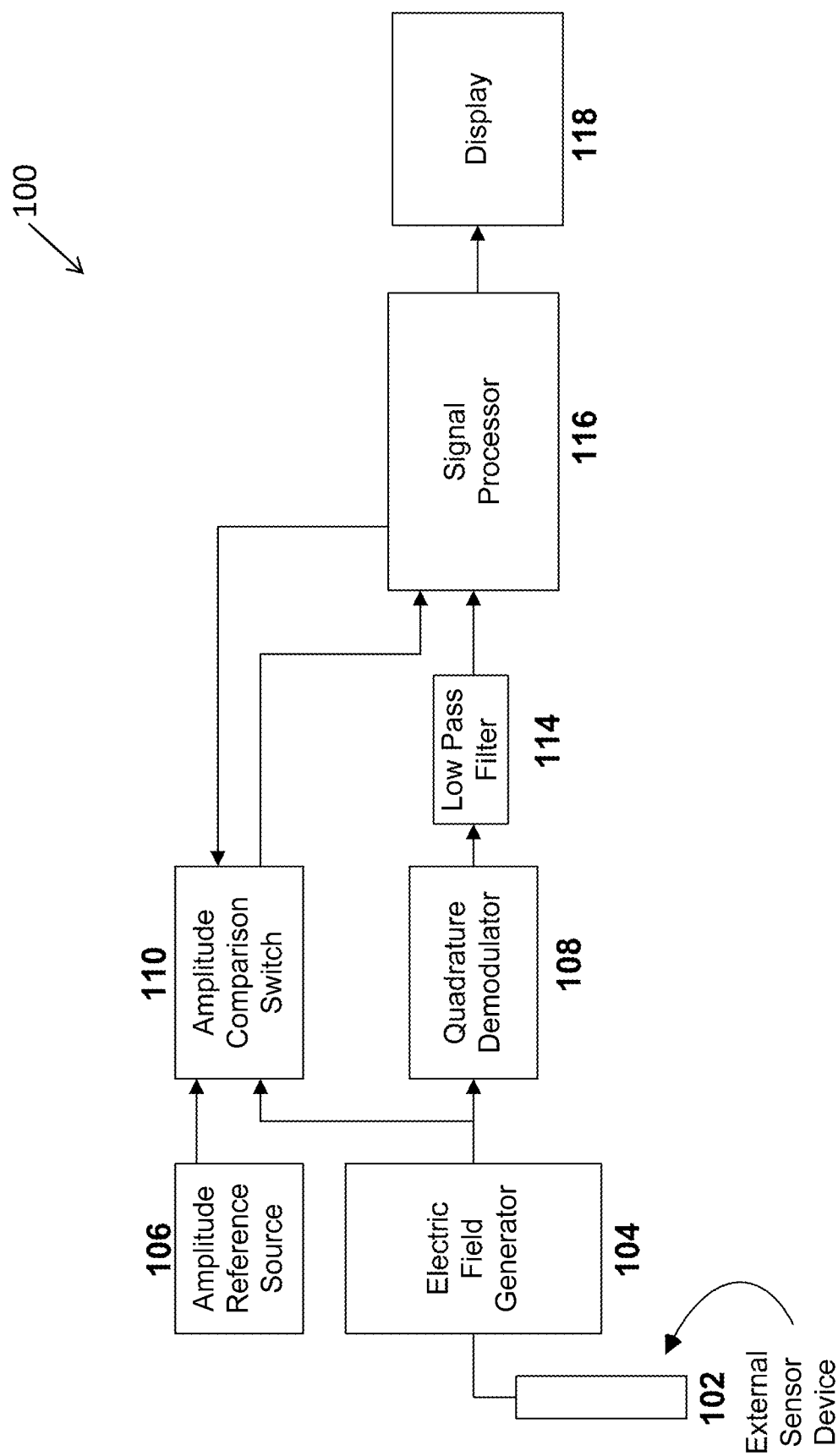
FIG. 1 illustrates a system for detecting and analyzing changes in a body according to certain embodiments of the present disclosure.

FIG. 1 illustrates a system 100 for detecting and analyzing changes in a body according to certain embodiments of the present disclosure. The system 100 includes an external sensor device 102, an electric field generator 104, an amplitude reference source 106, a quadrature modulator 108, an amplitude comparison switch 110, a low pass filter 114, a signal processor 116, and a display 118. The components included in the system 100 can be further broken down into more than one component and/or combined together in any suitable arrangement. Further, one or more components can be rearranged, changed, added, and/or removed. In some embodiments, one or more components of the system 100 can be made by an application specific integrated circuit (ASIC).

The electric field generator 104 creates an electric field that illuminates the desired area of detection. The frequency and amplitude of this electric field is determined by the characteristics of the body being observed. In some embodiments, a frequency-determining component of the electric field generator 104—a resonant circuit than can comprised of a combination of inductive, capacitive, and resistive elements—is connected to an external device that creates the electric field providing the desired coverage of the body of material being studied. In some embodiments, the electric field generator 104 can be an oscillator, such as an inductor-capacitor (LC) tank oscillator.

The external sensor device 102 may be made from a wide variety of materials; the only requirement of these materials is that they are electrical conductors. The external sensor device 102 can be constructed in many different mechanical configurations to provide appropriate coverage of the desired region. For example, in some embodiments, the external sensor device 102 can be a plurality of metallic plates. In some embodiments, the shape and/or the orientation of the external sensor device 102 can be changed as needed.

In some embodiments, the external sensor device 102 is not required to physically contact the body being studied. For example, the external sensor device 102 and the supporting electronics could be installed in the driver's seat of an over-the-highway truck to detect changes in physiological indicators of driver drowsiness and thus take actions to prevent an accident. In some embodiments, the sensing process usually is done separately in two paths: (1) in a first path the changes in the real component of the vector sum, e.g., energy dissipation, are detected; (2) in a second path the changes related to the imaginary component—a component such as a capacitance or inductance in which the phase of the current flowing in them is orthogonal to the current in the real component—are separately processed. In some embodiments, the changes in amplitude of the electric field are detected in the first path, and the changes in frequency of the electric field are detected in the second path. Generally, as known by a person skilled in the art, the changes in phase of the electric field can be obtained by analyzing the changes in frequency of the electric field. These two signals can be combined in later signal processing to re-create the changes in the complex permittivity or kept as individual signals for separate analysis. These two paths are discussed separately below.

Figure 6:
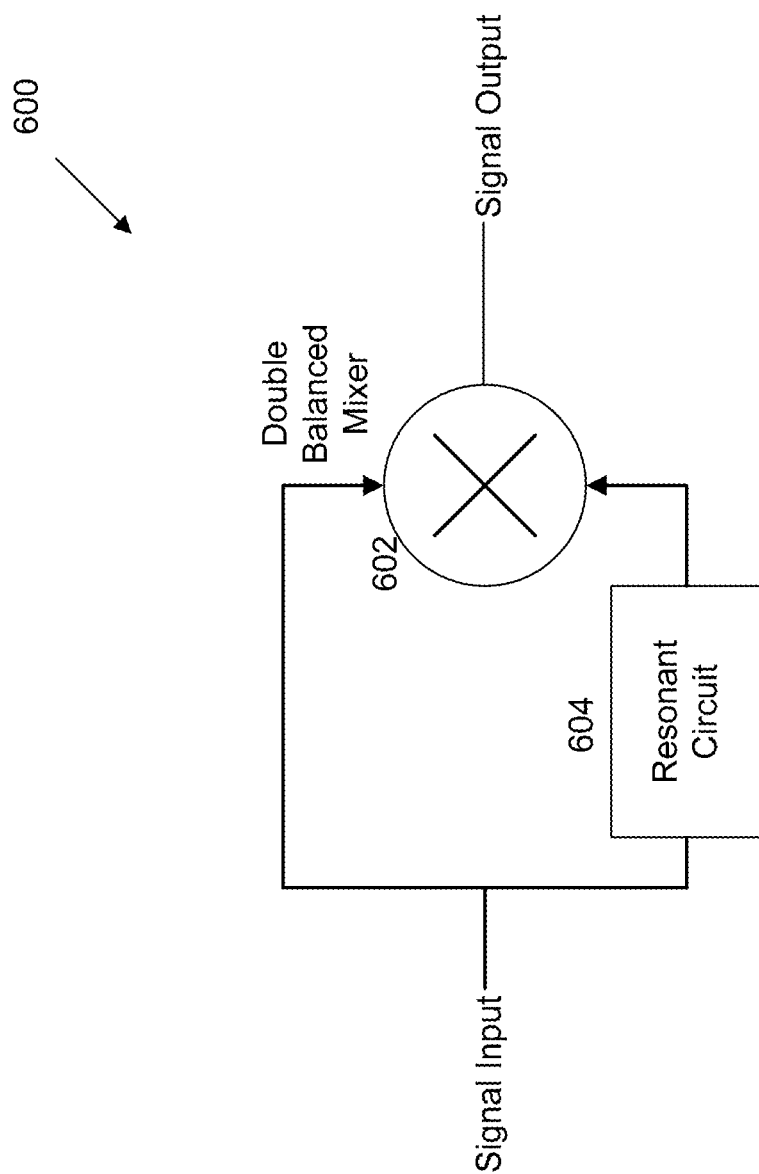
FIG. 6 illustrates a quadrature demodulator according to certain embodiments of the present disclosure.

To detect changes in the imaginary component of the complex permittivity, the output of the electric field generator 104 is connected to the quadrature demodulator 108. The quadrature demodulator 108 detects the changes of the frequency of the output of the electric field generator 104 and produce a detected response that includes a low frequency component and a high frequency component. FIG. 6 illustrates a quadrature demodulator 108 according to certain embodiments of the present disclosure. The quadrature demodulator 108 includes a mixer 602 and a resonant circuit 604. In the present disclosure, a double balanced mixer is described, but other suitable types of mixers can also be used. The components included in the quadrature demodulator 108 can be further broken down into more than one component and/or combined together in any suitable arrangement. Further, one or more components can be rearranged, changed, added, and/or removed.

An input signal to the quadrature demodulator 108 is split into two paths. One path is connected to one input port of the double balanced mixer 602, and the other path is connected to the resonant circuit 604. The output of the resonant circuit 604 is connected to the other input port of the double balanced mixer 602. In some embodiments, the resonant circuit 604 includes an inductor and a capacitor. In some embodiments, the resonant circuit 604 includes an inductor, a capacitor, and a resistor. The circuit components of the resonant circuit 604 can be connected in series, in parallel, or any other suitable configuration. The resonant circuit 604 can also be implemented by other circuit configurations that are appreciated by a person skilled in the art. In some embodiments, the resonant circuit 604 is tuned to the nominal center frequency of the electric field generator 104.

The double balanced mixer 602 multiplies the two signals together (one signal from the input and the other signal from the resonant circuit 604). The product of the two signals creates two components in the output: one proportional to the difference between the two input frequencies and another at the sum of the two input frequencies. When there is an exact 90-degree phase difference between the two signals, the demodulator output is zero. When the phase difference is less than about +/−90 degrees there will be a DC component in the output of the double balanced mixer 602.

The output signal from the quadrature demodulator 108 is fed to a low pass filter 114. The low pass filter 114 is typically an analog circuit that includes resistive, inductive and/or capacitive elements that separates the low frequency component of the quadrature modulator 108 from the much higher frequency component generated by the quadrature modulator 108. The cutoff frequency of the low pass filter is selected to provide low attenuation of the desired signal components while sufficiently suppressing the high frequency terms. After filtering, the signal is connected to the signal processor unit 116 described below.

Detecting changes in electric field dissipation is processed somewhat different from detecting frequency changes in electric field. In FIGS. 1 and 6, the output of the electric field generator 104 is multiplied by a phase-shifted version of itself produced by the resonant circuit 604. Unlike phase/frequency change detection, amplitude variations must be compared with the electric field generator 104 output unchanged by the material being studied. Referring again to FIG. 1, an amplitude reference signal is created by measuring the output of the electric field generator 104 in the absence of any external influence and used to set the output level of the amplitude reference source 106.

The amplitude reference source 106 is typically a time and temperature stable voltage reference that can be provided by a semiconductor component such as a diode. The output of the amplitude reference source 106 is fed to one input of the amplitude comparison switch 110. The switch 110, controlled by the signal processor 116, alternately connects the amplitude reference source 106 and electric field generator output 104 to the signal processor 116. By measuring the difference between the reference signal 106 and the electric field generator 104 output—and with sufficient calibration information—the amount of power absorbed, e.g., dissipated, by the material under study may be computed.

The amplitude comparison switch 110 functions by sampling the output of the electric field generator 104 at a rate at least twice as fast as the most rapid variation of the amplitude of the electric field generator 104 and subtracting the value of the amplitude reference source 106. The output of the amplitude comparison switch 110 is thus equal to the difference between the amplitude of the electric field generator 104 and the amplitude of the amplitude reference source 106.

The signal processor 116 takes the output of the low pass filter 114 and extracts the desired components into desired formats for further use or processing. The signal processor 116 also takes the output of the amplitude comparison switch 110 to analyze the changes in amplitude of the electric field. The signal processor 116 can be implemented by use of either analog, digital, or combined circuits.

Figure 7:
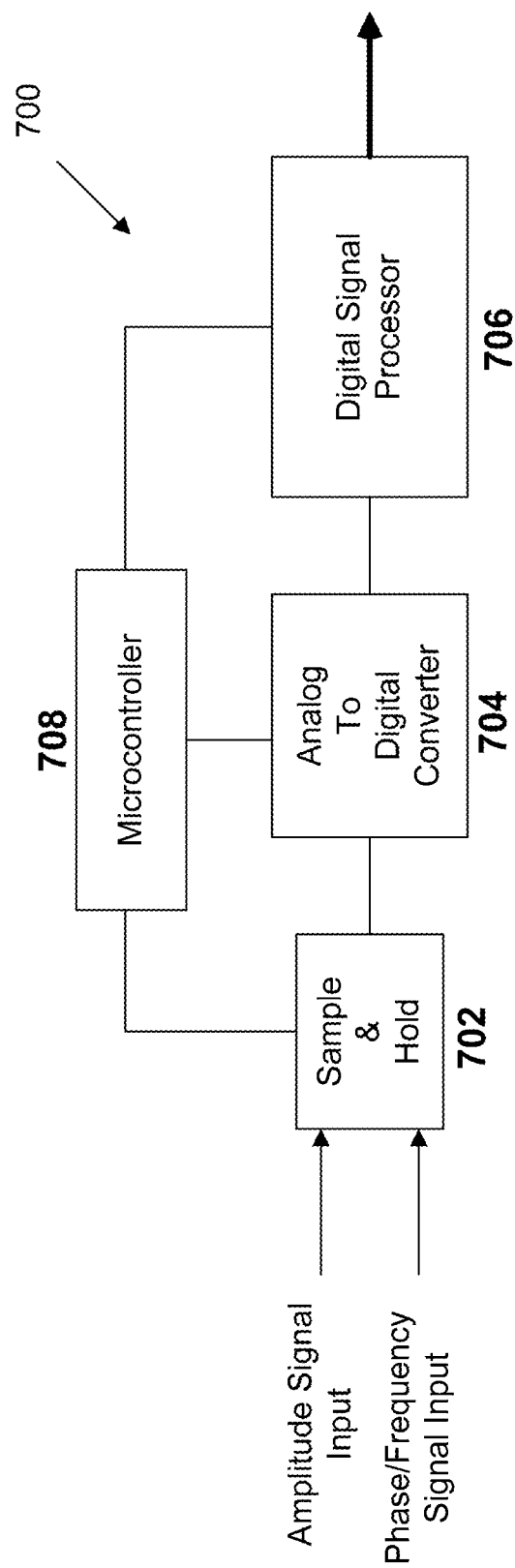
FIG. 7 illustrates a signal processor according to certain embodiments of the present disclosure.

FIG. 7 illustrates a signal processor 116 according to certain embodiments of the present disclosure. The signal processor 116 includes a sample-and-hold circuit 702, an analog-to-digital converter (ADC) 704, a digital signal processor 706, and a microcontroller 708. The components included in the signal processor 116 can be further broken down into more than one component and/or combined together in any suitable arrangement. Further, one or more components can be rearranged, changed, added, and/or removed.

The sample-and-hold circuit 702 is configured to sample a continuous-time continuous-value signal and hold the value for a specified period of time. A typical sample-and-hold circuit 702 includes a capacitor, one or more switches, and one or more operational amplifier. In some embodiments, other suitable circuit implementations can also be used.

The ADC 704 receives the output of the sample-and-hold circuit 702 and converts it into digital signals. In some embodiments, the ADC 410 can have a high resolution. Since the changes in bulk permittivity of the entire region within the electric field in many possible applications are expected to be relatively slow, e.g., less than a few hundred Hertz, in some embodiments it can be sufficient to undersample the output of the electric field generator 404 by using the sample-and-hold device 406 to make short samples that can be processed with the ADC 704 with a sample rate in the five thousand samples/sec range. An ADC with 24-bit resolution or 32-bit resolution are readily available. In some embodiments, the ADC 704 can have other suitable resolutions.

The digital signal processor 706 can be configured process the output of the ADC 704. In some embodiments, the digital signal processor 706 can be a microprocessor.

The microcontroller 708 can be coupled to one or more components of the signal processor 116. In some embodiments, the microcontroller 708 can control the sampling rate and/or clock rate of the one or more components of the signal processor 116. In some embodiments, the microcontroller 708 can issue command signals to the one or more components of the signal processor 116. In some embodiments, the microcontroller 708 can be a generic high performance low power system on chip (SOC) product. For example, the microcontroller 708 can be an ARM based processor, such as an ARM Cortex-M4 core processor or any other suitable models.

Referring to the display 118, the display 118 can be configured to display various results generated by the signal processor 116. The display 118 can be a touch screen, an LCD screen, and/or any other suitable display screen or combination of display screens. In some embodiments, the output of the signal processor 116 can also be fed to a data logger for signal storage and/or processing.

Figure 2:
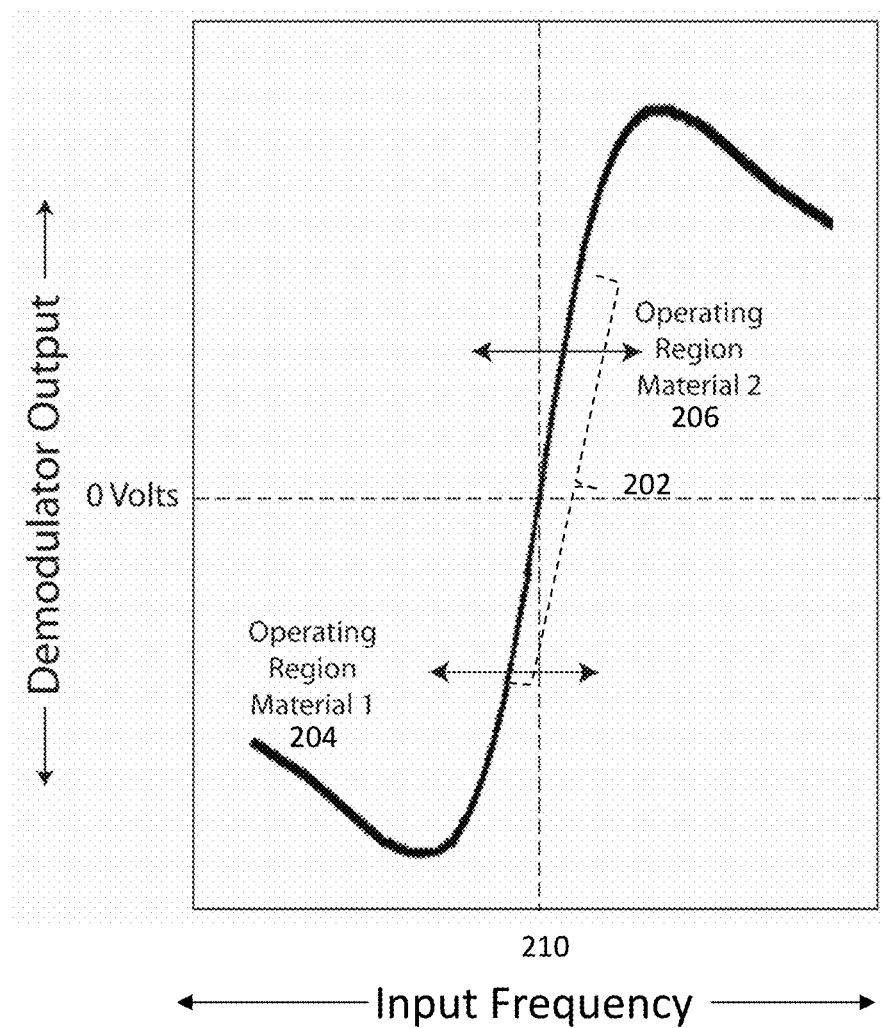
FIG. 2 illustrates a transfer function of a quadrature demodulator according to certain embodiments of the present disclosure.

FIG. 2 shows a generalized version of the transfer function of a quadrature demodulator 108 showing the typical relationship between the voltage output and frequency of the input signal from the electric field generator 104. The horizontal axis shows frequency of the input signal in Hertz (Hz), and the vertical axis shows demodulator output in Volts (V). The center of the horizontal axis 210 indicates the nominal resonant frequency of the resonant circuit 604. For example, if the nominal resonant frequency of the resonant circuit 604 is 80 MHz, then the center of the horizontal axis 210 is at 80 MHz. The slope of the central region 202 of the curve can be made quite linear to allow operation over an extended frequency range while offering the same sensitivity in terms of output voltage as function of phase/frequency change. The transfer function is mathematically dependent only on the frequency/phase relationship between the two inputs to the double-balanced mixer 108. This permits a wide and dynamic range in detection in the phase/frequency changes induced by material properties separate from changes in amplitude due to dissipative properties.

FIG. 2 illustrates the sensor operating as it might be employed in two different applications while using the same electric field generator 104 and the quadrature demodulator 108. In Region 1 204, the DC component—dependent on the exact value of the frequency and slope of the transfer function—might be, for example, −1.5 volts. If there are small variations in the frequency of the electric field generator 104, there will also be small variations in the quadrature demodulator output voltage. For the example here the output variations will be centered about −1.5 volts. In Region 2 206, the DC term might be, for example, around +1.0 volts. However, since the slope of the transfer function is very close to being the same in both regions, the small variations will be centered around 0 volts.

This is an important benefit to the approach taken here. If there are a wide variety of materials, each with varying electromagnetic properties within the electric field, the aggregated output of the quadrature demodulator 108 can have a mean DC level determined by the contributions of all materials within the electric field region, while still maintaining an essentially constant transfer function for small changes in material properties. The small-signal linearity allows signal components from separate constituents of the material being studied to be linearly combined. Linear combination of the various contributions in the output waveform can be readily separated in later signal processing. An example of a combined waveform showing both respiration and heart rate (pulse) signals is shown in FIG. 3.

Figure 3:
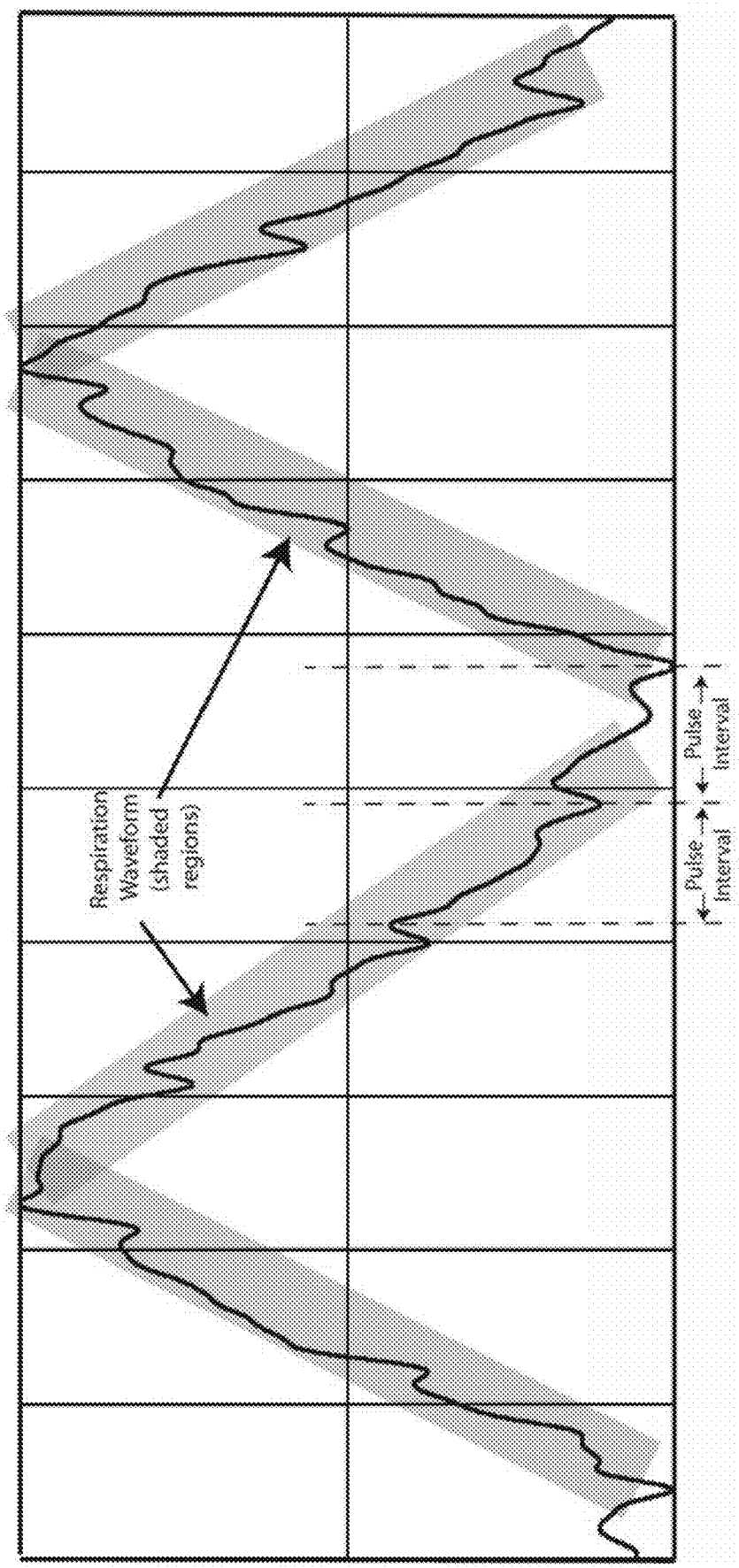
FIG. 3 illustrates a waveform combining both respiration and heart rate signals according to certain embodiments of the present disclosure.

FIG. 3 shows a signal comprised of a large, low frequency, roughly triangular waveform that might be typical of respiration by a body and a signal often seen in a heart pulse of smaller amplitude, higher frequency, and more complex waveform. In FIG. 3 the linear addition of these two waveforms is shown as the smaller amplitude, higher frequency, more complex heart pulse "riding" on the larger, slower triangular respiration component.

Figure 4:
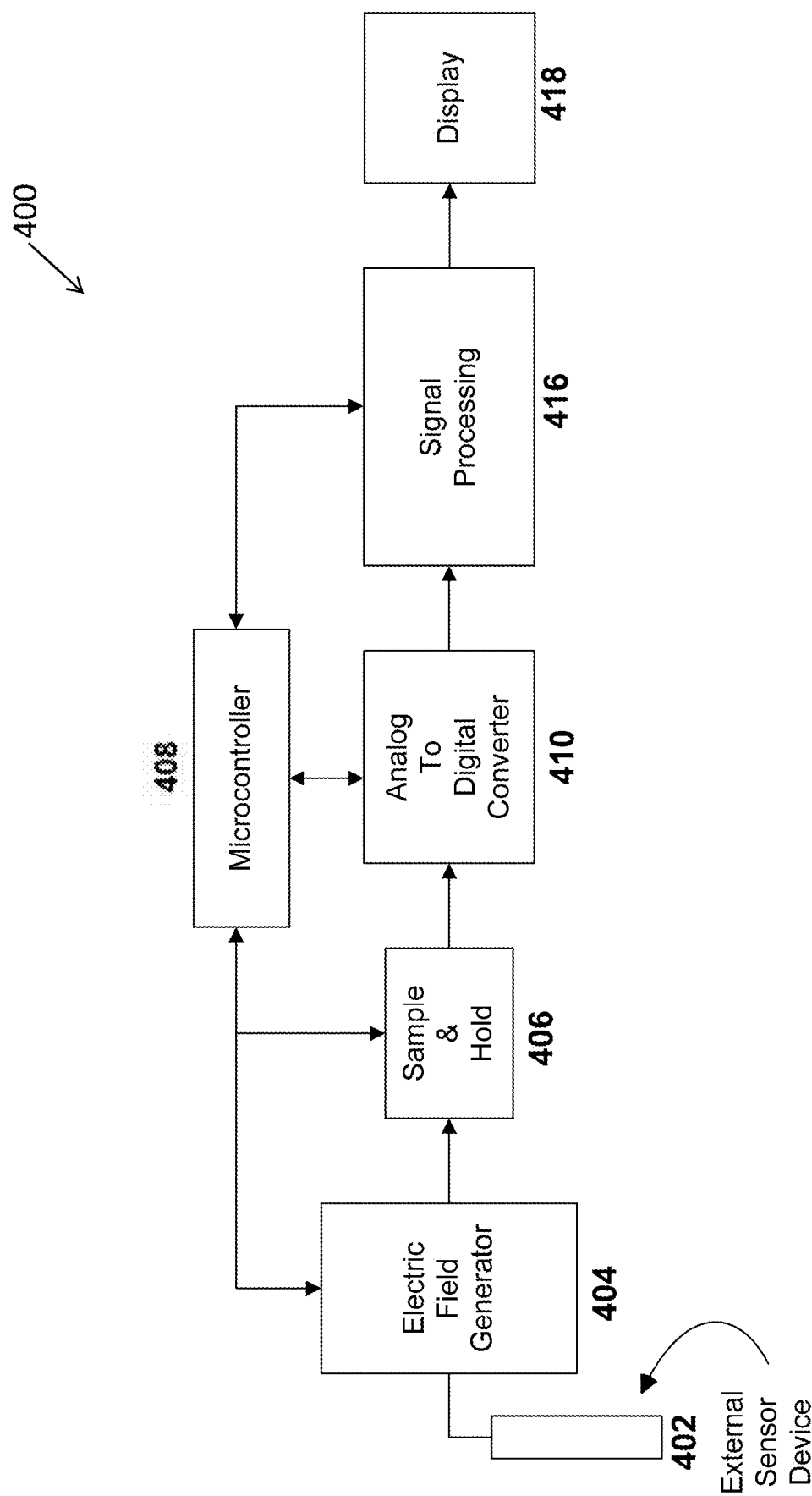
FIG. 4 illustrates a system for detecting and analyzing changes in a body according to certain embodiments of the present disclosure.

In addition to the largely analog design described above, a "direct-to-digital" approach is also possible. FIG. 4 illustrates a system 400 for detecting and analyzing changes in a body according to certain embodiments of the present disclosure. The system 400 includes an external sensor device 402, an electric field generator 404, a sample-and-hold device 406, a microcontroller 408, an ADC 410, a digital signal processor 416, and a display 418. The components included in the system 400 can be further broken down into more than one component and/or combined together in any suitable arrangement. Further, one or more components can be rearranged, changed, added, and/or removed. In some embodiments, the components included in FIG. 4 are similar to the corresponding components described in FIG. 1 and/or FIG. 7.

In some embodiments, the system 400 replaces most analog components described in FIG. 1 with digital or mixed-signal components. The "direct-to-digital" concept employs the ADC 410 driven by the sample-and-hold device 406. In some embodiments, the ADC 410 can have a high resolution. Since the changes in bulk permittivity of the entire region within the electric field in many possible applications are expected to be relatively slow, e.g., less than a few hundred Hertz, it can be sufficient to undersample the output of the electric field generator 404 by using the sample-and-hold device 406 to make short samples that can be processed with the ADC 410 with a sample rate in the five thousand samples/sec range. Such devices with 24-bit resolution are readily available, as are 32-bit versions at a significantly higher component price. In such a system, the signal processor 416 would take over the functions performed by the quadrature demodulator 108 described in FIG. 1. Since the features of the "direct-to-digital" instrument would be determined by the software in the signal processor 416, a single hardware set could be loaded with specialized software for different applications. The programmable characteristics of a "direct-to-digital" approach could enable economies of scale, driving down the unit cost and opening new market opportunities. In some embodiments, the ADC can be made by an application specific integrated circuit (ASIC).

Figure 5:
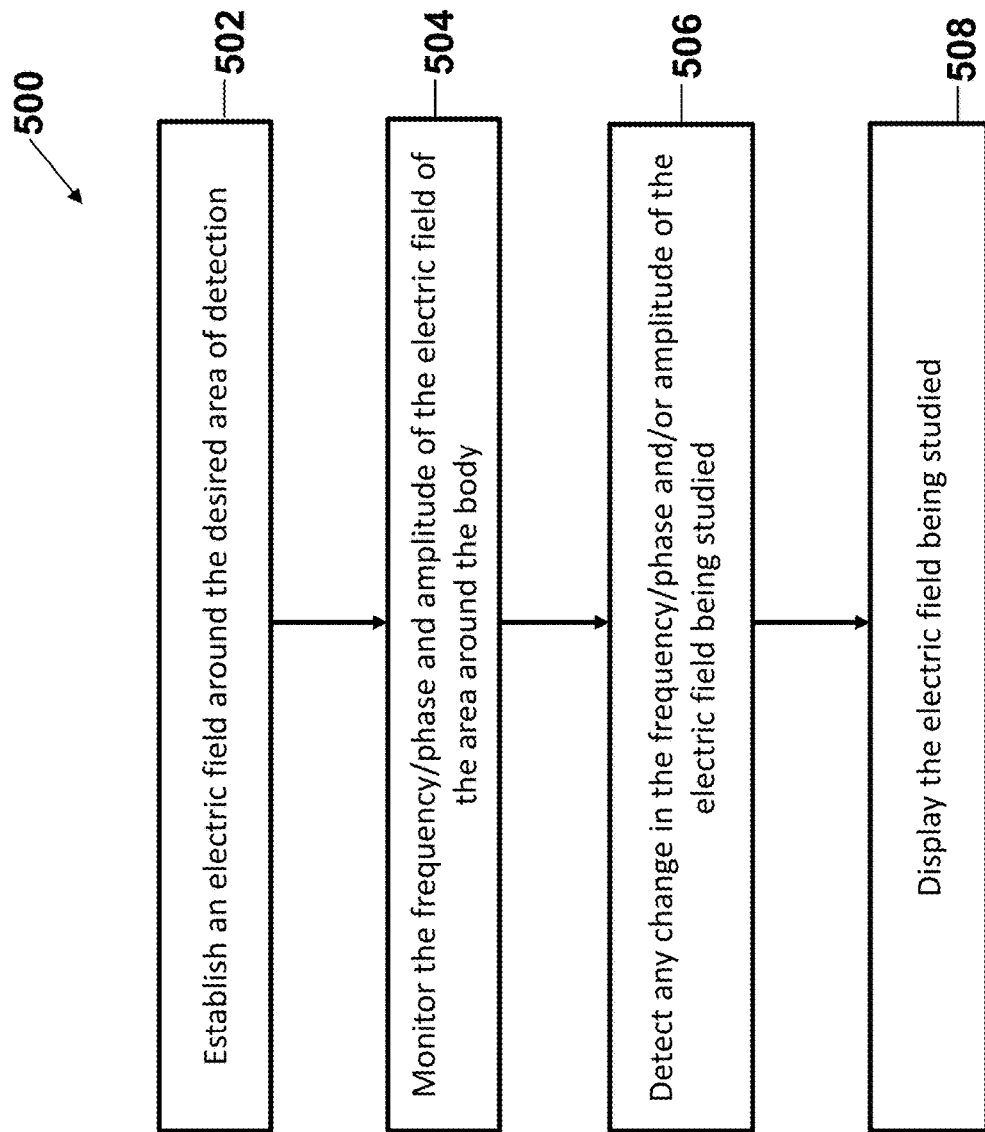
FIG. 5 illustrates a process of detecting and analyzing changes in a body according to certain embodiments of the present disclosure.

FIG. 5 is a flow chart illustrating a process 500 of detecting and analyzing changes in a body according to certain embodiments of the present disclosure. The process 500 is illustrated in connection with the system 100 shown in FIG. 1 and/or the system 400 shown in FIG. 4. In some embodiments, the process 500 can be modified by, for example, having steps rearranged, changed, added, and/or removed.

At step 502, an electric field is established around the desired area of detection. The desired area of detection is typically around a body that is going to be monitored. In some embodiments, the electrical field is established by using the electric field generator 104, which creates an electric field that illuminates the desired area of detection. The process 500 then proceeds to step 504.

At step 504, the frequency and amplitude of the electric field of the desired area of detection are monitored. In some embodiments, the external sensor device 102 is used to monitor the area around and within the body. The external sensor device 102 is not required to physically contact the body being studied. The process 500 then proceeds to step 506.

At step 506, the electric field of the desired area of detection is processed and analyzed to detect any change. The process 500 can detect the change of the electric field in both amplitude and frequency/phase. For example, amplitude variations of the electric field can be compared with the electric field generator 104 output unchanged by the material being studied. Referring again to FIG. 1, an amplitude reference signal is created by measuring the output of the electric field generator in the absence of any external influence and used to set the output level of the amplitude reference source 106. The output of the amplitude reference source 106 is fed to one input of the amplitude comparison switch 110. The switch 110, controlled by the signal processor 116, alternately connects the amplitude reference source 106 and electric field generator output 106 to the signal processor. By measuring the difference between the reference signal and the electric field generator 104 output—and with sufficient calibration information—the amplitude comparison response of the electric field can be determined.

The change of the electric field in frequency/phase can be detected and analyzed by the quadrature demodulator configuration discussed in connection with FIG. 1 and FIG. 6. For example, in some embodiments, the output of the electric field generator 104 is connected to the quadrature demodulator that is configured to detect the changes of the frequency of the output of the electric field generator 104 and produce a detected response that includes a low frequency component and a high frequency component. The detected response is then fed to a low pass filter 114 that is configured to filter out the high frequency component of the detected response to generate a filtered response. In some embodiments, once the changes in frequency is detected, the changes in phase can be readily derived by people skilled in the art.

The filtered response and the amplitude comparison response can then be supplied to a signal processor for further analysis.

In some embodiments, the change of the electric field can be analyzed under the "direct-to-digital" approach described in the system 400 in connection with FIG. 4. The output of the electric field generator 404 can be sampled and held by the sample-and-hold device 406 and digitized by the ADC 410. The digitized output of the ADC 410 can then be analyzed by the digital signal processor 416. The process 500 then proceeds to step 508.

At step 508, the electric field can be displayed for visual inspection. In some embodiments, the changes of the electric field can also be displayed and recorded. In some embodiments, the changes of the electric field can be extracted to provide specific bodily function features such as vascular processes and conditions, respiration processes and conditions, and other body material characteristics that vary with permittivity.

In some embodiments, the system 100 or the system 400 can include a processor, which can include one or more cores and can accommodate one or more threads to run various applications and modules. The software can run on the processor capable of executing computer instructions or computer code. The processor may also be implemented in hardware using an application specific integrated circuit (ASIC), programmable logic array (PLA), field programmable gate array (FPGA), or any other integrated circuit.

The processor can be couple with a memory device, which can be a non-transitory computer readable medium, flash memory, a magnetic disk drive, an optical drive, a PROM, a ROM, or any other memory or combination of memories.

The processor can be configured to run a module stored in the memory that is configured to cause the processor to perform various steps that are discussed in the disclosed subject matter.

In some embodiments, the electric field generator of the present invention has a tuner for adjusting the signal outputting to the quadrature demodulator. In some embodiments, the tuner can be implemented in an application-specific integrated circuit (ASIC), programmable logic array (PLA), field programmable gate array (FPGA), or any other integrated circuit. In some embodiments, the tuner can be implemented as a stand-alone subunit connected within or to the electric field generator. For example, the tuner can be an integrated inductor-capacitor (LC) tank oscillator.

Referring back to FIG. 2, a typical transfer function of a quadrature demodulator 108 depicts the relationship between the voltage output and frequency of the input signal from the electric field generator 104. The horizontal axis shows the frequency of the input signal in Hertz (Hz), and the vertical axis shows the demodulator output in Volts (V). The center of the horizontal axis 210 indicates the nominal resonant frequency of a resonant circuit. The slope of the central region 202 illustrates the linear frequency range of the electric field generated by the electric field generator. It may be sometimes desirable, or even necessary, to expand the linear frequency range of slope 202 in order to allow signal components from separate constituents of a material to be linearly combined. An advantage of linearly combining the various contributions is that the output waveform can be readily separated in later signal processing for individual analysis. In contrast, a signal component not in the linear frequency range cannot be linearly combined, and thus makes it challenging to analyze its individual contribution in the output waveform.

Figure 8:
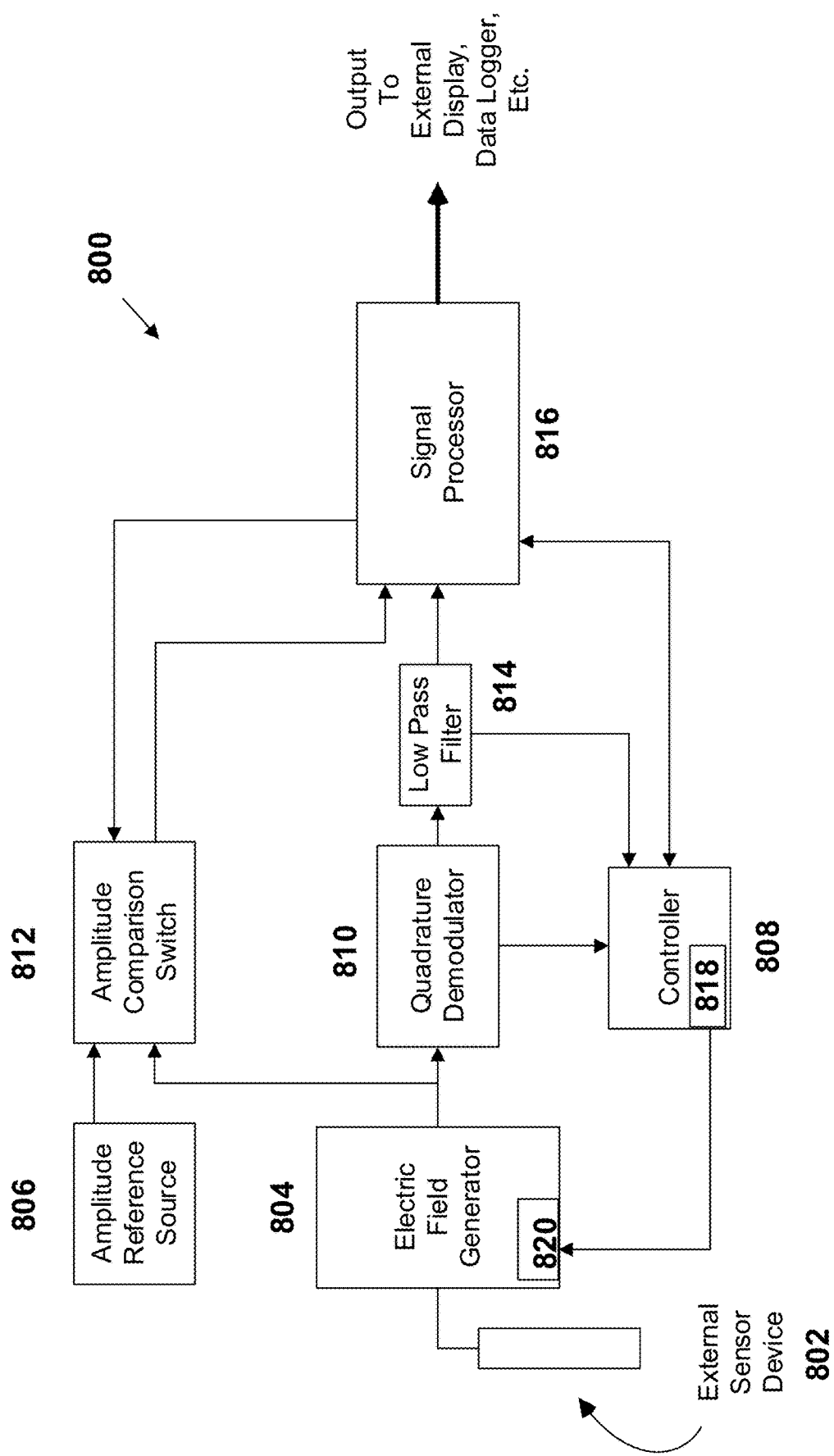
FIG. 8 illustrates a system for detecting and analyzing changes in a body according to certain embodiments of the present disclosure.

One of the ways to expand the linear frequency range of the quadrature demodulator is by adjusting the response curve of the quadrature demodulator. Such adjustment is possible because the quadrature demodulator's output voltage is related to the change of the oscillator frequency. However, adjusting the quadrature demodulator's output could decrease the sensitivity of the system. Alternatively, since the quadrature demodulator's output is a function of the change in frequency and not the actual frequency, shifting the actual frequency itself provides another way to expand quadrature demodulator's linear frequency range without sacrificing the sensitivity. For example, FIG. 8 illustrates a system 800 for detecting and analyzing changes in a body according to certain embodiments of the invention. The system 800 is capable of adjusting the quadrature demodulator's linear frequency range by tuning the electric field generator.

Referring to FIG. 8, the system 800 includes an external sensor device 802, an electric field generator 804 with a tuner 820, an amplitude reference source 806, a controller 808 with an adjuster 818, a quadrature modulator 810, an amplitude comparison switch 812, a low pass filter 814, and a signal processor 816 configured to output data to a display. The components included in the system 800 can be further broken down into more than one component and/or combined together in any suitable arrangement. Further, one or more components can be rearranged, changed, added, and/or removed. For example, in some embodiments, system 800 can detect and analyze physical changes in an object without the amplitude reference source 806, and amplitude comparison switch 812. In some embodiments, the system 800 establishes amplitude and/or frequency reference comparison using a specific feedback value.

In some embodiments, the electric field generator 804 is configured to generate an electric field based on the information received from the external sensor device 802 subject to adjustments made by the tuner 820. The external sensor device 802, connected to the field generator 804, is configured to detect physical changes in a body or an object in the electric field, and to output the sensor information to the electric field generator 804. The external sensor device 802 may be made from a wide variety of materials; the only requirement of these materials is that they are electrical conductors. To detect the imaginary component of the changes in the electric field, the output of the electric field generator 804 is connected to the quadrature demodulator 810. The quadrature demodulator 810 detects the changes of the frequency of the electric field and produces a detected response that includes a low frequency component and a high frequency component. In some embodiments, the detected response is fed to a low pass filter 814, and then send to the signal processor 816 for further analysis, similar to the process depicted in FIG. 1.

In some embodiments, the detected response from the quadrature demodulator 810 is fed to the controller 808 to establish a feedback loop for tuning the electric generator 804. The controller 808 can include one or more hardware processors, memory components, electronic circuits, and the like. For example, the controller 808 may include an ASIC. The controller 808 can include standalone components, components integrated with other features of system 800, or a combination thereof. In some embodiments, the controller 808 includes the adjuster 818 that is coupled to the tuner 820 of the electric field generator 804 to enable the system or a user to adjust the outputting signal of the electric field generator 804.

Referring to FIG. 8, the controller 808 may output a frequency control signal, via the adjuster 818, to the tuner 820 of the electric field generator 804 based on the detected response received from the quadrature demodulator 810. For example, if the detected response shows that a signal component from a constituent of a material is outside of the linear frequency range, the controller 808 can analyze the transfer function, and output a frequency control signal to the electric field generator 804 to adjust the electric field generator 804's output signal. In some embodiments, the actual frequency of the electric field is modified via the frequency control signal. In response, the quadrature the linear frequency range of the quadrature demodulator 810 may be expanded so that all signal components are within the linear frequency range. Although the feedback loop described here is based on the detected response form the quadrature demodulator 810, responses from other components in the system 800 may also be used. For instance, the feedback loop can also be established via the filtered response from the low pass filter 814, the analyzed response from the signal processor 816, or directly from the output of the electric field generator 804. In some embodiments, the feedback loop can receive signals from more than one component of the system 800.

The frequency control signal may be transmitted via any suitable communication media, including wired or wireless media. In some embodiments, the frequency control signal may include one or more analog electrical signals, digital electrical signals, electrical waveforms (e.g., pulse-width modulation waveforms), or the like.

In some embodiments, the electric field generator 804 includes components with different functions. For example, the electric field generator 804 can include an LC tank oscillator, a buffer, and a power conditioning element. In some embodiments, the LC tank oscillator is configured as a Colpitts oscillator or any other suitable oscillator; the buffer is a unity gain device that shields the LC tank oscillator from undesired interactions with the quadrature demodulator 810; and the power condition element insures a stable power value for the LC tank oscillator and the buffer. The Colpitts oscillator can be the electric field generator 804's tuner 820. In operation, the controller 808 may send a frequency control signal to adjust the values of the inductor (L) and/or capacitor (C) of the Colpitts oscillator such that the signal entering the quadrature modulator 810 will always be within the linear limits of the quadrature demodulator 810's linear frequency range. Different types of variable inductor or capacitor may be used in the Colpitts oscillator. In some embodiments, the values of the L and C can be adjusted by combining the fixed values of L and of C with one or more of electrically sensitive inductive and/or capacitive components. Hence, by altering the electricity flowing through at least one of the electrically sensitive inductive or capacitive components, the controller 808 can effectively change the values of L or C, and thus modify the signal entering the quadrature modulator 810. In some embodiments, the flow of electricity is controlled by manually adjusting an electric source. In some embodiments, the flow of electricity can be automatically controlled by a voltage circuit.

Figure 9:
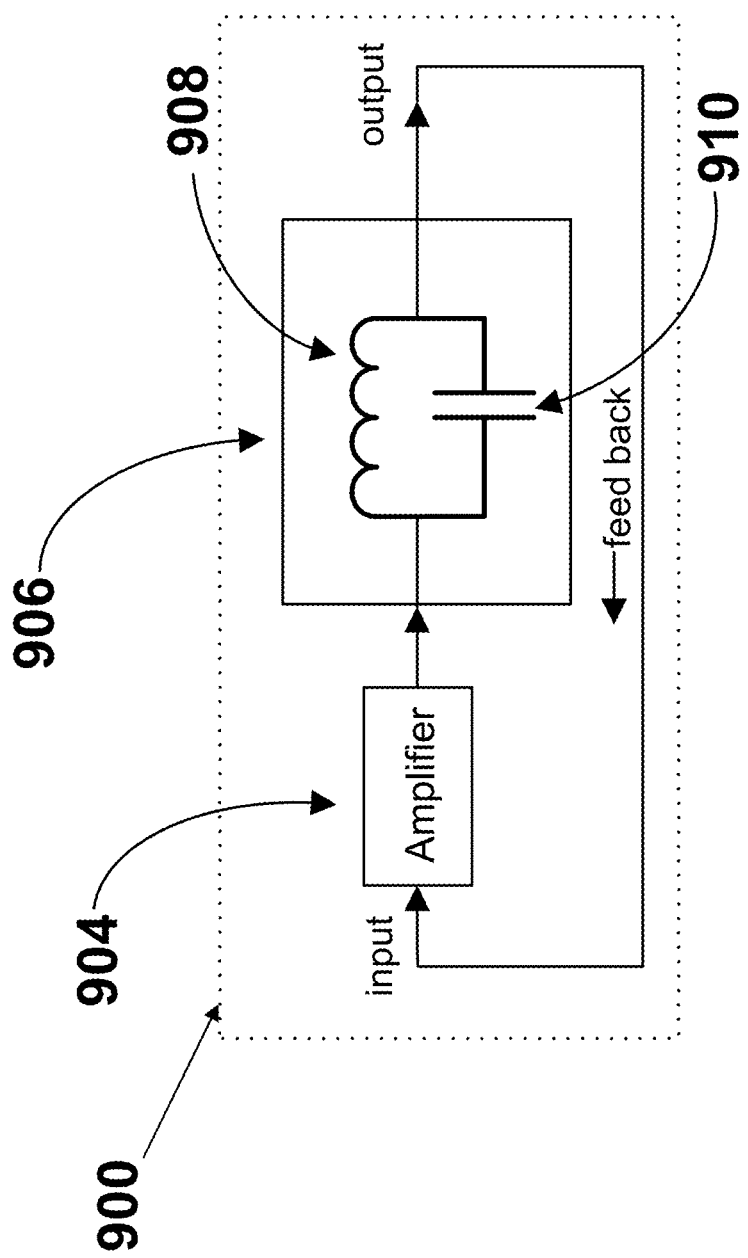
FIG. 9 illustrates an inductor-capacitor (LC) tank oscillator according to certain embodiments of the present disclosure.

FIG. 9 illustrates a Colpitts oscillator 900 according to certain embodiments of the invention. The Colpitts oscillator 900 includes two main components: an amplifier 904 and a resonant tank circuit 906. Colpitts oscillators are known for their ability to output signals with a fixed frequency. According to certain embodiments, the Colpitts oscillator 900 is initialized when a small input, usually random noise, that is received by the amplifier 904. The amplifier 904 increases the magnitude of the initial small input and sends an amplified signal to the resonant tank circuit 906 which includes an inductive element 908 and a capacitive element 910. The input and output of the resonant tank circuit 910 are configured to only allow signals to pass through with a single frequency. Hence, the amplified signal can only enter and exit the resonant tank circuit 906 with a single frequency. The output of the resonant tank circuit 906 is then fed back to the input of the amplifier 904 to via feedback loop. In operation, the feedback process would continue so long as the amplifier has sufficient gain to overcome any losses in the resonant tank circuit 906. The feedback process enables the Colpitts oscillator to reliability output signals with a fixed frequency.

According to certain embodiments, the electric field generator 804 with Colpitts oscillator as its tuner can be tuned by a frequency control signal from the controller 808. Specifically, the frequency of oscillation, measured in Hertz, is defined by $$\frac{1}{\sqrt{LC}},$$

where L is me inductive component measured in Henries and C is the capacitive component measured in Farads. Referring to FIG. 9, to tune the electric field generator 804, the frequency control signal would adjust the value of the inductive 908 and capacitive component 910 in the resonant tank circuit 906. In some embodiments, the inductive and capacitive components can be combined with multiple constituents. For example, the inductive component 908 may be a single device of fixed inductance while the capacitive component 910 might be implemented as two separate devices—one with a fixed value and the other a variable capacitor. As another example, the capacitive component 910 may be a single device of fixed capacitance while the inductive component 908 might be implemented as two separate devices—one with a fixed value and the other as a variable inductor. In some embodiments, the variable capacitor may be a varactor—a type of diode which changes capacitance with voltage application. However, other variable capacitors that can change the capacitance with application of voltage are also within the scope of the invention. In some embodiments, the variable inductor may be a microelectromechanical system (MEMS) variable inductor. However, other variable inductors that can change the inductance with application of voltage are also within the scope of the invention.

As mentioned above, in some embodiments the system 800 can automatically tune the frequency of the electric field generated via a feedback loop. For example, the controller 808 may send the frequency control signal based on a voltage received from the quadrature demodulator 810. In other embodiments, the controller 808 may send the frequency control signal based on one or more voltages received from the low pass filter 814, the signal processor 816, the electric field generator 801, and/or other components of the system 800.

In some embodiments, the controller 808 can tune the electric field generator 804 without receive any response from the quadrature demodulator 810, the low pass filter 814, the signal processor 816, or other components of the system 800. An operator may manually adjust the knobs on the controller to tune the LC tank oscillator based on his or her observation of the data from any components in system 800. Other manual adjustment techniques and mechanisms are also within the scope of the invention.

In some embodiments, the controller 808 can sample the detected response from the quadrature modulator 810 to determine other changes in the frequency not caused by the LC tank oscillator. In this regard, the controller 808 can hold the variable components of the LC tank oscillator constant, and act as a monitoring system for detecting other frequency changing variables. For example, the controller 808 may pick up frequency changes caused by the external sensor device 802. In some embodiments, the monitored information can be fed directly to the signal processor 816 for analysis or for outputting to an external display.

Figure 10:
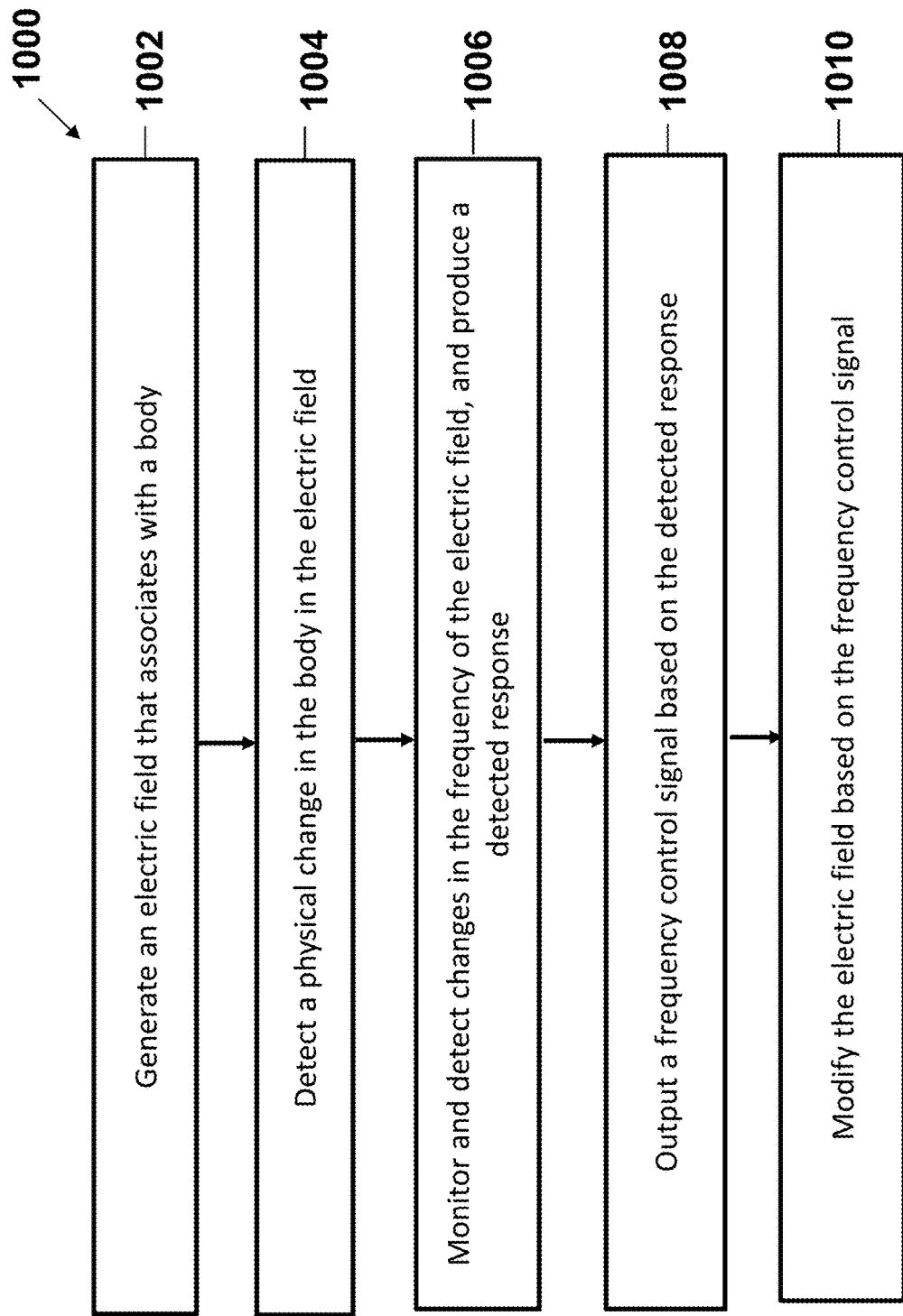
FIG. 10 illustrates a process of detecting and analyzing changes in a body according to certain embodiments of the present disclosure.

FIG. 10 is a flow chart illustrating a process 1000 of detecting and analyzing changes in a body according to certain embodiments of the present disclosure. The process 1000 is illustrated in connection with the system 800 shown in FIG. 8. In some embodiments, the process 1000 can be modified by, for example, having steps rearranged, changed, added, and/or removed.

At step 1002, an electric field associated with the body is generated. The body need not be the whole body, it can be a specific part of the body. In some embodiments, the electrical field is generated by using the electric field generator 804, which creates an electric field that illuminates a desired area of detection. The process 1000 then proceeds to step 1004.

At step 1004, a physical change in the body is detected in the electric field generated in step 1002. In some embodiments, the external sensor device 802 is used to monitor the area around and within the body. The external sensor device 802 is not required to physically contact the body being studied. The process 1000 then proceeds to step 1006.

At step 1006, changes in the frequency of the electric field is detected and monitored, and a detected response is produced. In some embodiments, the quadrature modulator 806 is used to monitor and detect the frequency change of the electric field. Referring to FIG. 8, in some embodiments, frequency changes are reflected in the transfer function of the quadrature demodulator 806, where the transfer function shows the relationship between the voltage output and the frequency of the input signal from the electric field generator 804. In some embodiments, the detected response is subsequently send to one or more other components for further analysis or processing. In some embodiments, the detected response is sent to a component not depicted in FIG. 8. In some embodiments, the detected response is sent to the controller 808. In some embodiments, the detected response is initially sent to another component such as the low pass filter 814, before passing on to the controller 808. The process 1000 then proceeds to step 1008.

At step 1008, a frequency control signal is outputted to a component for modifying the frequency of the electric field. In some embodiments, the adjuster 818 of the controller 808 is used to output the frequency control signal. And the electric field generator 804 is used to receive the frequency control signal. Referring back to FIG. 8, although in some embodiments the output of the controller 808 is fed directly to the input of the electric field generator 804, other communication paths are also possible. For example, the frequency control signal can be routed to another component not depicted in FIG. 8 before arriving at the electric field generator 804. In some embodiments, the frequency control signal is received by the tuner 820 of the electric field generator 804. In some embodiments, the frequency control signal is received by another component or circuit within the electric field generator 804 (not shown in FIG. 8). The process 1000 then proceeds to step 1010.

At step 1010, an electric field generated by the electric field generator is modified based on the frequency control signal. In some embodiments, the electric field being modified is the electric field generated in step 1002. In some embodiments, the electric field being modified is another electric field generated after step 1002. According to certain embodiments, the tuner 820 modifies the electric field based on the frequency control signal. In some embodiments, another component or circuit within the electric field generator (not shown) can modify the electric field based on the frequency control signal. In some embodiments, another component, not necessary in the system 800, can receive the frequency control signal and modify the electric field accordingly. In some embodiments, the process 1000 ends at step 1010. In some embodiments, the system 800 repeats the process 1000 multiple times to achieve a proper adjustment.

The following applications and/or methods are non-limiting examples of applying the disclosed subject matter.

In some embodiments, changes in capacitor excitation frequency can be remotely sensed to alleviate the need for analog data reduction at the sensor.

In some embodiments, blood pressure can be measured by isolating a body region using a pressure "doughnut" and then releasing pressure and monitoring the return of blood flow as a result. Traditional means enclosing a limb to close an artery and monitor the pressure at which the artery opens up as the pressure is released. With the disclosed invention, a body region can be determined that excludes blood by closing capillaries (within the 'doughnut' pressure region) and monitoring the pressure at which they then open again. This simplification of application could then be applied to in-seat circumstances in hospital/clinic waiting rooms and the like.

In some embodiments, first derivatives can be used to find a recurring pattern in a combined time series signal of heartbeat and respiration such that the respiration signal can be subtracted from the combined signal to leave the heartbeat signal.

In some embodiments, the mathematical notion of Entropy (H) can be used to analyze a heartbeat signal and extract event timing information with respect to characterizing heart processes.

In some embodiments, wavelet analysis can be used to disambiguate complex time series data with highly variable frequency compositions. Signals that vary their frequency in time are resistant to effective analysis using traditional digital techniques such as fast Fourier transform (FFT). Wavelets provide the notion of short pattern correlation that can be applied to a sliding window of time series data in order to provide a second correlation time series that indicates the time at which a test pattern or "wavelet" is found within the first time series.

In some embodiments, a low resolution FFT can be used to peak search for power levels in a correlation function. This FFT power analysis is then used to set the correlation cutoff level and thus determine higher resolution correlated frequencies based on the power levels provides by the FFT. The FFT essentially filters out correlations below a particular power level so that more strongly correlated signals can remain. This provides a way of efficiently 'normalizing' the power levels relative to one another in trying to separate low frequency signals that are relatively close in frequency but widely separated in power without having to increase the resolution of the FFT with attendant significantly increased FFT window acquisition time.

In some embodiments, Kalman filters can be used to process the effect of changes in permittivity as indicated by a time series data such that the filter relates the predicted next value in a time series in maintaining a useable moving average for the purposes of normalizing a highly variable signal from a sensor with high dynamic range.

In some embodiments, measurement of the temperature of a body or substance can be obtained by measuring the permittivity of said body or substance where such permittivity may be correlated to temperature.

In some embodiments, measurement of the pressure within a body, substance, and/or liquid can be obtained by measuring the permittivity of said body, substance, and/or liquid where such permittivity may be correlated to pressure.

In some embodiments, stress levels in an individual can be determined by analyzing his or her motion, heartbeat characteristics and respiration using a remote, non-contact, biometric sensor.

In some embodiments, the quality of food in food processing and handling operations can be monitored by correlating the qualities of the food to the measured permittivity of the food item.

In some embodiments, the characteristics (e.g., turbulence, flow, density, temperature) of a fluid (e.g., paint, blood, reagents, petroleum products) can be monitored by correlating the characteristics of the fluid to the objective characteristics of the fluid.

In some embodiments, cavities and/or impurities in solid materials can be found. Such application can be used in areas such as the detection of delamination in composite materials, voids in construction materials, entrained contaminants, and/or the quality of fluid mixing.

In some embodiments, contraband enclosed within solid objects can be found.

In some embodiments, the life signs of infants in cribs, pushchairs and/or car seats can be monitored.

In some embodiments, the presence and life signs located in automobiles can be detected for the purposes of providing increased passenger safety, deploying airbags, and/or prevent baby from being left behind.

In some embodiments, the sentience of a driver can be detected by using heartbeat variability. In some embodiments, gestures such as the head-nod signature motion.

In some embodiments, the life signs in unauthorized locations (e.g., smuggling and/or trafficking) can be discovered.

In some embodiments, the quality of glass manufacture can be assessed by detecting variations in thickness, poor mixing, and/or the entrainment of impurities and/or.

In some embodiments, the nature of underground/subsurface texture and infrastructure (pipes and similar) can be assessed.

In some embodiments, the external sensor device disclosed herein can be combined with other sensors (e.g., camera, echolocation, pressure/weight/accelerometers) to provide enhanced sensor application using sensor "fusion."

In some embodiments, certain body conditions can be detected. The body conditions include conditions of the body relating to heart-lung functions, pulmonary fluid levels, blood flow and function, large and small intestine condition and process, bladder condition (full/empty) and process (rate fill/empty), edema and related fluid conditions, bone density measurement, and any other suitable condition or combination of conditions.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, systems, methods, and media for carrying out the several purposes of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

What is claimed:

1. A system to detect and analyze changes in a body, comprising:
   an electric field generator configured to generate an electric field;
   an external sensor, coupled to the electric field generator, configured to detect a physical change in the body in the electric field, wherein the physical change affects frequency of the electric field;
   a frequency change detector, coupled to the electric field generator, configured to detect changes in the frequency of the electric field generated by the electric field generator and to produce a detected response;
   a controller, coupled to the electric field generator, configured to:
      receive the detected response; and
      output a frequency control signal to the electric field generator to modify the frequency of the electric field.

2. The system of claim 1, wherein the outputted frequency control signal is part of a feedback loop.

3. The system of claim 2, wherein the feedback loop further comprises the detected response.

4. The system of claim 2, further comprising:
   a low pass filter that receives information from the frequency change detector, the low pass filter configured to filter out a high frequency component of the detected response to generate a filtered response,
   wherein the feedback loop comprises the filtered response.

5. The system of claim 1, further comprising:
   a tuner configured to:
      receive the frequency control signal; and
      modify the frequency of the electric field generated by the electric field generator.

6. The system of claim 1, wherein the changes in the frequency of the electric field are caused by physiological events within the body that comprise one or more of a heart rate, a respiration rate, a blood pressure, or a fluid level.

7. The system of claim 6, wherein the detected response comprises contributions from a respiration rate signal and a heart rate signal; and
   wherein the system further comprises a signal processor configured to separate the heart rate signal from the respiration rate signal.

8. The system of claim 1, wherein the controller is further configured to:
   determine that a signal component from a material of the body is outside of a linear frequency range of the frequency change detector; and
   output the frequency control signal to the electric field generator to expand the linear frequency range of the frequency change detector by modifying the frequency of the electric field.

9. A method to detect and analyze changes in a body, the method comprising:

generating, by an electric field generator, an electric field that associates with the body;

detecting, by a sensor device, a physical change in the body in the electric field, wherein the physical change affects frequency of the electric field;

detecting, by a frequency change detector, changes in the frequency of the electric field and producing a detected response;

receiving, by a controller, the detected response;

outputting, by the controller, a signal to modify the frequency of the electric field associated with the body.

10. The method of claim 9, wherein the outputted frequency control signal is part of a feedback loop.

11. The method of claim 10, wherein the feedback loop further comprises the detected response.

12. The method of claim 10, further comprising:
filtering out a high frequency component of the detected response to generate a filtered response,
wherein the feedback loop further comprises the filtered response.

13. The method of claim 9, further comprising:
modifying, by a tuner, the frequency of the electric field generated by the electric field generator based at least on the frequency control signal.

14. The method of claim 9, wherein the changes in the frequency of the electric field are caused by physiological events within the body that comprise one or more of a heart rate, a respiration rate, a blood pressure, or a fluid level.

15. The method of claim 14, wherein the detected response comprises contributions from a respiration rate signal and a heart rate signal; and
wherein the method further comprises separating the heart rate signal from the respiration rate signal.

16. The method of claim 9, further comprising:
determining that a signal component from a material of the body is outside of a linear frequency range; and
outputting a signal to the electric field generator to expand the linear frequency range of the frequency change detector by modifying the frequency of the electric field.

17. A non-transitory computer readable medium storing executable instructions operable to cause a processor to perform operations comprising:
receiving, as a first part of a feedback loop, a detected response from a frequency change detector coupled to an electric field generator that generates an electric field, the frequency change detector configured to detect changes in the frequency of the electric field caused by physiological events within a body in the electric field and produce the detected response;
detecting, using the detected response, the physiological events within the body; and
outputting, as a second part of the feedback loop, a frequency control signal to a tuner of the electric field generator to modify the frequency of the electric field.

18. The non-transitory computer readable medium of claim 17, wherein the operations further comprise:
filtering out a high frequency component of the detected response to generate a filtered response,
wherein the feedback loop further comprises the filtered response.

19. The non-transitory computer readable medium of claim 17, wherein the physiological events within the body comprise one or more of a heart rate, a respiration rate, a blood pressure, or a fluid level.

20. The non-transitory computer readable medium of claim 17, wherein the operations further comprise:
determining that a signal component from a material of the body is outside of a linear frequency range; and
outputting a signal to the electric field generator to expand the linear frequency range of the frequency change detector by modifying the frequency of the electric field.

* * * * *